«12» United States Patent [19]
Nakano et al.

[11] Patent Number: 5,571,530
[45] Date of Patent: Nov. 5, 1996

[54] PERCUTANEOUS PREPARATION OF TULOBUTEROL

[75] Inventors: Yoshihisa Nakano; Tetsuo Horiuchi; Sanae Fujiwara; Senji Unozawa, all of Osaka, Japan

[73] Assignees: Nitto Denko Corporation, Osaka; Hokuriku Seiyaku Co., Ltd., Fukui, both of Japan

[21] Appl. No.: 279,070

[22] Filed: Jul. 22, 1994

Related U.S. Application Data

[63] Continuation of Ser. No. 20,439, Feb. 22, 1993, abandoned, which is a continuation of Ser. No. 454,829, Dec. 22, 1989, abandoned.

[30] Foreign Application Priority Data

Dec. 23, 1988 [JP] Japan ................................. 63-327242
Sep. 22, 1989 [JP] Japan ................................... 1-247629

[51] Int. Cl.$^6$ ................................................... A61K 9/70
[52] U.S. Cl. ........................................... 424/448; 424/449
[58] Field of Search ................................. 424/448, 449

[56] References Cited

U.S. PATENT DOCUMENTS 4,420,470 12/1983 Otsuka et al. .......................... 424/449
4,623,346 11/1986 Von Bittera et al. .................... 424/449
4,814,168 3/1989 Sablotsky .............................. 424/449
5,254,348 10/1993 Hoffman et al. ........................ 424/449

FOREIGN PATENT DOCUMENTS 0033615 8/1981 European Pat. Off. .
0156080 10/1985 European Pat. Off. .
0288734 1/1988 European Pat. Off. .
0259136 9/1988 European Pat. Off. .
0306926 3/1989 European Pat. Off. .
0374980 6/1990 European Pat. Off. .
63-10716 1/1988 Japan .

OTHER PUBLICATIONS

Patent Abstracts of Japan, vol. 12, No. 209 (C–504)[3056], 15th Jun. 1988.
Communication–European Search Report EP 89 12 4028.

*Primary Examiner*—Amy Hulina
*Attorney, Agent, or Firm*—Sughrue, Mion, Zinn, Macpeak & Seas

[57] ABSTRACT

A percutaneous preparation of tulobuterol is disclosed, comprising a support having thereon a base layer comprising a pressure-sensitive adhesive containing tulobuterol, the pressure-sensitive adhesive comprising polyisobutylene. The preparation achieves persistent and effective administration of tulobuterol through the skin into the body.

3 Claims, No Drawings

PERCUTANEOUS PREPARATION OF TULOBUTEROL

This is a continuation of application Ser. No. 08/020,439 filed Feb. 22, 1993, now abandoned, which was a continuation of application Ser. No. 07/454,829, filed Dec. 22, 1989, now abandoned.

FIELD OF THE INVENTION

This invention relates to a preparation for percutaneously administering β-receptor stimulating tulobuterol for prolonged relief of obstructive disorders of airway, such as bronchial asthma, chronic bronchitis, and bronchitis with asthma.

BACKGROUND OF THE INVENTION

Tulobuterol acts selectively at a $\beta_2$-receptor of the sympathetic nervous system to relax the bronchial smooth muscles and is widely employed for the treatment of chronic obstructive diseases of respiratory organs, and particularly bronchial asthma. It is generally administered through oral routes as tablets or a dry syrup.

Although tulobuterol is of longer duration than other β-stimuli, it is still insufficient when orally administered and, in some cases, fails to suppress or prevent attacks at night. In particular, it produces no satisfactory effect on an asthmatic attack frequently occurring at dawn.

Under this situation, tulobuterol preparations which maintain a therapeutic blood level of tulobuterol for a prolonged time have been demanded. In this connection, an external preparation for percutaneous absorption of tulobuterol has recently been proposed as disclosed in JP-A-63-10716 (the term "JP-A" as used herein means an "unexamined published Japanese patent application"). This preparation has a novel dosage form including an ointment and a cream and aims to eliminate an undesirable temporary rise of tulobuterol blood level observed in oral administration. However, though the external preparation is expected to exhibit long-acting efficacy as compared with conventional oral tablets, the active ingredient in applied ointments or creams is wiped away with clothing, making it difficult to strictly control the dosage. Further, sufficient studies are not devoted to adhesive preparations which can be easily applied under dose control with relative ease, and references to adhesives for use in adhesive preparations are no more than general description about natural rubbers or acrylic resins. In the working examples, only an adhesive preparation using a polyacrylic ester as a base polymer is examined with no thorough consideration given to important factors in medical preparations, such as efficacy and stability of an active ingredient and skin irritation at the damaged part on peeling.

Usage of adhesive preparations as a novel dosage form is also disclosed in JP-A-51-104021, JP-A-54-20129 (JP-B-62-14526), and JP-A-56-125311. All the preparations according to these publications comprise an adhesive base containing polyisobutylene as a base polymer having essentially incorporated thereinto a mineral oil as only a carrier for dissolution and release of the active ingredient and, therefore, may have a fear that the stability of the active ingredient is reduced with time due to interaction between the active ingredient and the mineral oil or impurities in the mineral oil. Further, use of a liquid mineral oil as a carrier makes release of the active ingredient very fast, thus giving rise to problems such that a sudden rise of the blood level causes side effects and that long duration characteristic of adhesive preparations is impaired. Thus, the above-described base containing a mineral oil cannot be preferable.

SUMMARY OF THE INVENTION

An object of this invention is to eliminate the above-described disadvantages associated with the conventional tulobuterol preparations and to provide a percutaneous preparation of tulobuterol by which the active ingredient is persistently and effectively absorbed through the skin to manifest excellent pharmaceutical effects.

Other objects and effects of this invention will be apparent from the following description.

The inventors have conducted extensive investigations to achieve the above purpose. As a result, the inventors have found that polyisobutylene, which is a synthetic rubber, is a suitable adhesive base for holding tulobuterol and for adhesion to the skin. It has been ascertained that the preparation comprising polyisobutylene directly containing tulobuterol exhibits improved sustained release and improved stability of tulobuterol without using other carriers for holding and releasing the active ingredient, such as mineral oils. It has also turned out that incorporation of a thermoplastic resin into such an adhesive base further prolongs release of tulobuterol, thus decreasing the number of doses, which leads to alleviation of skin irritation. The present invention has been completed based on these findings.

The present invention therefore provides a percutaneous preparation of tulobuterol comprising a support having thereon a base layer comprising a pressure-sensitive adhesive containing tulobuterol, the pressure-sensitive adhesive comprising polyisobutylene.

DETAILED DESCRIPTION OF THE INVENTION

The pressure-sensitive adhesive which can be used in the present invention comprises polyisobutylene, and preferably a mixture of two or more kinds of polyisobutylene selected from the group consisting of (a) polyisobutylene having a viscosity-average molecular weight of from 500 to 4,000, (b) polyisobutylene having a viscosity-average molecular weight of from 10,000 to 200,000, and (c) polyisobutylene having a viscosity-average molecular weight of from 900,000 to 2,100,000.

Polyisobutylene (a) provides to a base layer preferable softness and adhesion, polyisobutylene (c) provides to a base layer preferable cohesion and satisfactory release of the active ingredient, and polyisobutylene (b) provides moderate properties given by (a) and (c).

From the standpoint of active ingredient releasing properties and adhesion to the skin, the pressure-sensitive adhesive preferably contains from 10 to 80% by weight, more preferably from 20 to 50% by weight, of polyisobutylene (c), and from 0 to 80% by weight, preferably from 10 to 60% by weight, of polyisobutylene (a) and from 0 to 90% by weight, preferably from 10 to 80% by weight, of polyisobutylene (b), all based on the total weight of the pressure-sensitive adhesive.

The polyisobutylene used in this invention include a so-called butyl rubber comprising polyisobutylene as a major component and a small amount of an isoprene rubber. That is the butyl rubber may also be used as the polyisobutylene to sufficiently accomplish the purpose of this invention.

The pressure-sensitive adhesive of the present invention preferably contains a thermoplastic resin. The thermoplastic resin incorporated into the base layer in combination functions to properly hinder diffusion and migration of tulobuterol in the base layer to resulting persistent and efficient release of tulobuterol to the skin. Tulobuterol thus released under control is percutaneously absorbed into the body for a prolonged period of time to exhibit long-acting efficacy.

Examples of the thermoplastic resins which can be used in combination include thermoplastic resins which are crystalline at room temperature and have a softening point between 50° C. and 250° C., for example, tackifiers, such as rosin and its derivatives, terpene resins, terpene-phenol resins, petroleum resins, alkyl phenol resins, and xylene resins. These resins may be used either individually or in combination of two or more thereof. The thermoplastic resins are generally used in an amount of not more than 50% by weight, and preferably from 5 to 40% by weight, based on the total weight of the pressure-sensitive adhesive.

The pressure-sensitive adhesive comprising polyisobutylene contains tulobuterol in a dissolved or dispersed state, and the base layer comprising the adhesive also functions as a release controlling layer, by which tulobuterol is persistently released to the skin by diffusion and migration and successively absorbed into the body. Tulobuterol in the pressure-sensitive adhesive is gradually diffused and migrated therein and thus exhibits pharmaceutical effects for an extended period of time.

Tulobuterol as an active ingredient is preferably present in the base layer in a dissolved or dispersed state in an amount of from 1 to 50% by weight, and preferably from 5 to 20% by weight, based on the total weight of the base layer. If the content is less than 1% by weight, which sufficient efficacy or sustained manifestation of efficacy cannot be expected. If it exceeds 50% by weight, not only is expected any further improvement in efficacy and duration, but also there results an unfavorable tendency that the adhesion of the base layer to the skin is reduced.

Supports which can bemused in the percutaneous preparation of the present invention are not particularly limited. The support used in this invention preferably has softness so as not to cause considerable adverse feeling to the skin. Suitable examples of such supports include films of synthetic resins, e.g., polyethylene, polypropylene, polyester, polyvinyl acetate, an ethylene-vinyl acetate copolymer, polyvinyl chloride, and polyurethane; metallic foils, e.g., an aluminum foil and a tin foil; nonwoven fabric, cloth, paper; either singly or as a laminated film thereof. In order to enhance anchor effect to the base layer, the side of the support on the base layer is performed to a corona discharge treatment, a plasma treatment, an oxidation treatment, and the like.

While the percutaneous preparation according to the present invention basically comprises the support having provided thereon the above-described base layer, it is desirable to keep the surface of the base layer protected before use with a releasing liner, such as paper or a synthetic resin film coated with a release agent, e.g., a silicone resin and a fluorine-containing resin.

Since the percutaneous preparation of the present invention is of adhesive type to allow tulobuterol contained therein to be persistently supplied into the circulating blood through the skin., the active ingredient does not undergo metabolism due to a first pass through the liver as is encountered when orally administered, and also side effects due to a temporary rise in tulobuterol blood level does not occur. Thus, the bioavailability of tulobuterol in the preparation can be increased to accomplish an efficient administration of tulobuterol to the body.

The base layer containing tulobuterol comprises a pressure-sensitive adhesive of a simple composition mainly containing polyisobutylene with no percutaneous penetration enhancer or the like. Neither does it contain any carrier for dissolving and releasing of the active ingredient, e.g., mineral oils, as used in the conventional adhesive preparations. Hence, interaction between the base layer and tulobuterol is minimized and thereby the stability of the active ingredient with time is markedly improved.

Further, where a thermoplastic resin is incorporated into the pressure-sensitive adhesive, it functions as a hindrance to diffusion and migration of tulobuterol to further improve persistent release properties, whereby the effective blood level of the active ingredient can be maintained for a prolonged period of time. As a result, the number of doses (number of applications per unit time) can be decreased to reduce skin irritation.

The present invention is now illustrated in greater detail by way of Examples, but it should be understood that the present invention is not construed as being limited thereto. All the percents and parts are given by weight unless otherwise indicated.

EXAMPLE 1

In toluene were dissolved 37.5 parts of polyisobutylene having a viscosity-average molecular weight of 990,000 ("VISTANEX MML-80" produced by EXXON CHEMICAL JAPAN LTD.) as polyisobutylene (c), 12.5 parts of polyisobutylene having a viscosity-average molecular weight of 40,000 ("HIMOL 4H" produced by NIPPON PETROCHEMICALS COMPANY LTD.) as polyisobutylene (b), and 50 parts of polyisobutylene having a viscosity-average molecular weight of 1260 ("HV-300" produced by NIPPON PETROCHEMICALS COMPANY LTD.) as polyisobutylene (a), to prepare a 25.0% polyisobutylene solution. Tulobuterol was mixed with the polyisobutylene solution, and the mixture was coated on a releasing liner to a dry thickness of-40 μm and dried to form a base layer having a tulobuterol content of 10%.

The thus formed base layer was transferred to a 12 μm thick polyester film to obtain a percutaneous preparation.

EXAMPLE 2

A percutaneous preparation was prepared in the same manner as in Example 1, except that the base layer had a tulobuterol content of 20%.

EXAMPLE 3

A percutaneous preparation was prepared in the same manner as in Example 1, except for using a 25.0% polyisobutylene solution prepared by dissolving 25.0 parts of polyisobutylene having a viscosity-average molecular weight of 990,000 "VISTANEX MML-80" as polyisobutylene (c) and 75.0 parts of polyisobutylene having a viscosity-average molecular weight of 40,000 "HIMOL 4H" as polyisobutylene (b) in hexane (Tulobuterol content in base layer: 5%).

COMPARATIVE EXAMPLE 1

A percutaneous preparation was prepared in the same manner as in Example 1, except for using a mineral oil-containing polyisobutylene solution which was prepared by mixing the same polyisobutylene solution as used in Example 1 with a mineral oil in the same amount as the solid content in the solution (Tulobuterol content in base layer: 10%).

COMPARATIVE EXAMPLE 2

A tulobuterol preparation for oral administration (tablets each containing 1 mg of tulobuterol) was used as a comparative preparation.

COMPARATIVE EXAMPLE 3

Sixty parts of 2-ethylhexyl acrylate, 40 parts of 2-methoxyethyl acrylate, and 0.2 part of benzoyl peroxide were placed in a flask to conduct a polymerization reaction in an inert gas atmosphere.

During the polymerization, the reaction temperature was maintained at about 60° C. by controlling the stirring speed and the outer bath temperature and by dropwise addition of ethyl acetate as a solvent. About 12-hour reaction produced an acrylic ester copolymer solution having a solid content of 28.0%.

A percutaneous preparation was obtained in the same manner as in Example 1, except for using the thus prepared copolymer solution in place of the polyisobutylene solution (Tulobuterol content in base layer: 10%).

Each of the preparation specimens having an area of 5 cm$^2$ obtained in Examples 1 to 3 and Comparative Examples 1 and 3 was applied to the skin, and two tablets of Comparative Example 2 were orally administered. Tulobuterol blood levels at prescribed time after the percutaneous or oral administration were determined by gas chromatography. The results obtained are shown in Table 1 below.

TABLE 1

| Example No. | Blood Level (ng/ml) | | | | |
|---|---|---|---|---|---|
| | 2 Hrs. | 4 Hrs. | 8 Hrs. | 12 Hrs. | 24 Hrs. |
| Example 1 | 0.68 | 1.80 | 2.35 | 1.66 | 1.29 |
| Example 2 | 1.22 | 3.42 | 5.17 | 4.15 | 2.70 |
| Example 3 | 0.30 | 1.12 | 1.93 | 1.10 | 0.52 |
| Comparative Example 1 | 1.91 | 3.28 | 1.04 | 0.32 | 0.04 |
| Comparative Example 2 | 2.00 | 1.58 | 0.55 | 0.21 | ND* |
| Comparative Example 3 | 0.43 | 1.36 | 2.04 | 1.30 | 0.71 |

Note:
*Not detected.

Further, each of the preparations was sealed in an aluminum package and preserved at 40° C. for prescribed periods of time, and stability of the preparation was evaluated by determining the percent remain of tulobuterol. The results obtained are shown in Table 2.

TABLE 2

| Example No. | Remain of Tulobuterol (%) | | | |
|---|---|---|---|---|
| | 1 Month | 2 Months | 3 Months | 6 Months |
| Example 1 | 98.9 | 99.0 | 98.7 | 98.0 |
| Example 2 | 99.2 | 99.1 | 98.9 | 99.0 |
| Example 3 | 97.5 | 97.7 | 98.0 | 97.6 |

TABLE 2-continued

| Example No. | Remain of Tulobuterol (%) | | | |
|---|---|---|---|---|
| | 1 Month | 2 Months | 3 Months | 6 Months |
| Comparative Example 1 | 98.1 | 97.5 | 94.2 | 90.1 |
| Comparative Example 2 | 99.9 | 99.8 | 99.6 | 99.3 |
| Comparative Example 3 | 95.3 | 90.5 | 87.7 | 81.4 |

EXAMPLE 4

In hexane were dissolved 28.5 parts of polyisobutylene having a viscosity-average molecular weight of 990,000 "VISTANEX MML-80" as polyisobutylene (c), 43 parts of polyisobutylene having a viscosity-average molecular weight of 60,000 "HIMOL 6H" as polyisobutylene (b), 8.5 parts of polyisobutylene having a viscosity-average molecular weight of 1260 "HV-300" as polyisobutylene (a), and 20 parts of an alicyclic petroleum resin having a softening point of 100° C. ("Arkon P-100" produced by ARAKAWA CHEMICAL INDUSTRIES, LTD.) to prepare an adhesive solution having a solid content of 30.0%.

To the adhesive solution was added tulobuterol, and the composition was coated on a releasing liner to a dry thickness of 40 μm and dried to form a base layer.

The base layer was transferred to a 25 μm thick polyester film to obtain a percutaneous preparation (Tulobuterol content in base layer: 10%).

EXAMPLE 5

A percutaneous preparation was prepared in the same manner as in Example 4, except that the tulobuterol content in the base layer was 20%.

EXAMPLE 6

A percutaneous preparation (Tulobuterol content in base layer: 10%) was prepared in the same manner as in Example 4, except for using a 30.0% adhesive solution prepared by dissolving 33.5 parts of polyisobutylene having a viscosity-average molecular weight of 1,200,000 "VISTANEX MML-100" as polyisobutylene (c), 33.5 parts of polyisobutylene having a viscosity-average molecular weight of 40,000 "HIMOL 4H" as polyisobutylene (b), 16.5 parts of polyisobutylene having a viscosity-average molecular weight of 1260 "HV-300" as polyisobutylene (a), and 16.5 parts of an alicyclic petroleum resin having a softening point of 105° C. ("Escorez 5300" produced by EXXON CHEMICAL JAPAN LTD.) in hexane.

EXAMPLE 7

A percutaneous preparation was prepared in the same manner as in Example 4, except that the alicyclic petroleum resin was not used (Tulobuterol content in base layer: 10%).

The preparations obtained in Examples 4, 6, and 7 were cut to a size of 10 cm$^2$ and the preparation of Example 5 was cut to a size of 5 cm$^2$. Each cut piece was applied to the skin, and two tablets of Comparative Example 2 were orally administered. Tulobuterol blood levels at prescribed time after the percutaneous or oral administration were determined by gas chromatography. The results obtained are shown in Table 3 below.

TABLE 3

| Example No. | Blood Level (ng/ml) | | | | | | |
|---|---|---|---|---|---|---|---|
| | 2 Hrs | 4 Hrs | 8 Hrs | 12 Hrs | 24 Hrs | 48 Hrs | 72 Hrs |
| Example 4 | 0.20 | 0.40 | 2.00 | 2.12 | 2.09 | 1.86 | 1.19 |
| Example 5 | 0.19 | 0.86 | 1.86 | 1.93 | 2.22 | 2.01 | 1.45 |
| Example 6 | 0.16 | 0.38 | 1.95 | 2.03 | 2.15 | 1.53 | 1.06 |
| Example 7 | 0.97 | 2.82 | 5.09 | 4.82 | 1.03 | 0.43 | ND |
| Comparative Example 2 | 2.00 | 1.58 | 0.55 | 0.21 | ND | — | — |

Note:
ND: not detected.

The effective blood level of tulobuterol is from 1 to 3 ng/ml. It is therefore understood from the above results that, by the percutaneous preparation of tulobuterol of this invention, the active ingredient is persistently and effectively absorbed through the skin to exhibit excellent pharmaceutical effects.

While the invention has been described in detail and with reference to specific embodiments thereof, it will be apparent to one skilled in the art that various changes and modifications can be made therein without departing from the spirit and scope thereof.

What is claimed is:

1. A percutaneous preparation of tulobuterol consisting of a support having thereon a base layer consisting of a pressure-sensitive adhesive containing tulobuterol, wherein the tulobuterol is present in an amount of from 1 to 50% by weight based on the total weight of the base layer, and wherein said pressure-sensitive adhesive consists of a mixture of (i) from 10 to 80% by weight, based on the amount of said pressure-sensitive adhesive, of polyisobutylene having a viscosity-average molecular weight of from 900,000 to 2,100,0.00,, and (ii) at least one polyisobutylene selected from the group consisting of (a) from 0 to 80% by weight, based on the amount of said pressure-sensitive adhesive, of polyisobutylene having a viscosity-average molecular weight of from 500 to 4,000, and (b) from 0 to 90% by weight, based on the amount of said pressure-sensitive adhesive, of polyisobutylene having a viscosity-average molecular weight of from 10,000 to 200,000.

2. A percutaneous preparation of tulobuterol as claimed in claim 1, wherein said pressure-sensitive adhesive contains from 20 to 50% by weight of polyisobutylene having a viscosity-average molecular weight of from 900,000 to 2,100,000, from 10 to 60% by weight of polyisobutylene having a viscosity-average molecular weight of from 500 to 4,000, and from 10 to 80% by weight of polyisobutylene having a viscosity-average molecular weight of from 10,000 to 200,000, all based on the total weight of said pressure-sensitive adhesive.

3. A percutaneous preparation of tulobuterol as claimed in claim 4, wherein the amount of tulobuterol is from 5 to 20% by weight based on the total weight of said base layer.

* * * * *

UNITED STATES PATENT AND TRADEMARK OFFICE
CERTIFICATE OF CORRECTION

PATENT NO.   : 5,571,530
DATED        : November 5, 1996
INVENTOR(S)  : Nakano et al It is certified that error(s) appears in the above-identified patent and that said Letters Patent is hereby corrected as shown below:

Column 3, line 41, delete "bemused" and insert therefor -- be used--.

Column 3, line 65, delete "skin.," and insert therefor --skin,--.

Column 4, line 44, delete "-40" and insert therefor --40--.

Claim 1, line 10, delete "2,100,0.00,," and insert therefor --2,100,000,--.

Claim 3, line 2, delete "4" and insert therefor --1--.

Signed and Sealed this

Eighteenth Day of February, 1997

Attest:

BRUCE LEHMAN

*Attesting Officer*      *Commissioner of Patents and Trademarks*